United States Patent [19]

Isbey, Jr.

[11] Patent Number: 4,501,363
[45] Date of Patent: Feb. 26, 1985

[54] SURGICAL KIT

[76] Inventor: Edward K. Isbey, Jr., 407 Vanderbilt Rd., Asheville, N.C. 28803

[21] Appl. No.: 545,211

[22] Filed: Oct. 25, 1983

[51] Int. Cl.³ .................. B65D 85/62; B65D 81/36
[52] U.S. Cl. ................................ 206/570; 206/363; 206/514; 206/560; 206/564; 220/408
[58] Field of Search .......... 206/570, 363, 514, 560; 220/457, 306, 408

[56] References Cited

U.S. PATENT DOCUMENTS

| | | | |
|---|---|---|---|
| 3,412,888 | 11/1968 | Andrews et al. | 220/457 |
| 4,105,121 | 8/1978 | Mascetti | 220/306 |
| 4,226,328 | 10/1980 | Beddow | 220/408 |

Primary Examiner—William T. Dixson, Jr.
Attorney, Agent, or Firm—David M. Carter

[57] ABSTRACT

There is provided an improved surgical kit, including a pair of trays, one of which is adapted to be received inside of the other. Each tray includes a plurality of embossments in its bottom for receiving various surgical supplies. After the completion of the surgery the inner tray is adapted to be flipped over and applied as a top to the outer tray with various post-operative materials contained therein.

15 Claims, 5 Drawing Figures ns in which:
SURGICAL KIT

BACKGROUND OF THE INVENTION

This invention relates to surgical kits. More particularly, it relates to disposable surgical trays which house various surgical and postoperative supplies and is particularly adapted for use in optomological surgery.

In order to reduce the cost of cleaning and sterilizing reusable medical devices and supplies, the industry has been utilizing disposables in many instances. Surgical supplies are no exception. In ophthalmological cataract surgery for intraocular lens implantation a kit is being utilized for providing the disposable parts and accessories for an irrigation and aspiration surgical unit. The kit includes a first tray mounted within a second tray with the kit being covered on top with a sterile cover. The first tray, which is the inner tray, includes a raised embossed section which contains the small accessory parts utilized during the surgery. The inner tray also includes a deep pan section which is divided down the middle with a raised shoulder and contains larger plastic surgical accessories. The second tray or outer tray provides no apparent function other than as a protection for the inner tray against mechanical abuse. The above-described kit does not provide for any pre-operative or operative medications or solutions or any postoperative medications, solutions or materials. Normally, postoperative materials, such as eye pads, tape, eye cleaning solutions, etc. are given to the patient in a separate container placed in a box in an unorganized fashion. Therefore, there exists a need for a surgical kit which integrates both surgical supplies and post operative supplies in the same apparatus.

OBJECTS OF THE INVENTION

It is therefore one object of this invention to provide an improved surgical kit.

It is another object to provide a surgical kit which integrates both surgical supplies and postoperative supplies.

It is still another object to provide a surgical kit which is useful to both the surgeon during surgery and to the patient after surgery.

SUMMARY OF THE INVENTION

In accordance with one form of this invention there is provided an improved surgical kit having first and second trays. Each tray has side walls and a bottom. The bottom of each tray has a plurality of embossments for receiving various medical supplies. The first tray has a lip extending away from its side walls about the outer periphery of the first tray. The second tray has a shoulder on its side walls about the inner periphery of the second tray. The shoulder of the second tray receives the lip of the first tray such that the first tray is mounted on the second tray. Prior to the surgery the first tray is received inside of the second tray. After the surgery the first tray is flipped over and forms a top for the second tray. Postoperative materials may be placed inside the container formed by the first and second trays and given to the patient upon completion of the surgery.

BRIEF DESCRIPTION OF THE DRAWINGS

The subject matter which is regarded as the invention is set forth in the appended claims. The invention itself, however, together with further objects and advantages thereof may be better understood by referring to the following description taken in conjunction with the accompanying drawings in which:

DESCRIPTION OF THE PREFERRED EMBODIMENT

Figure 1:
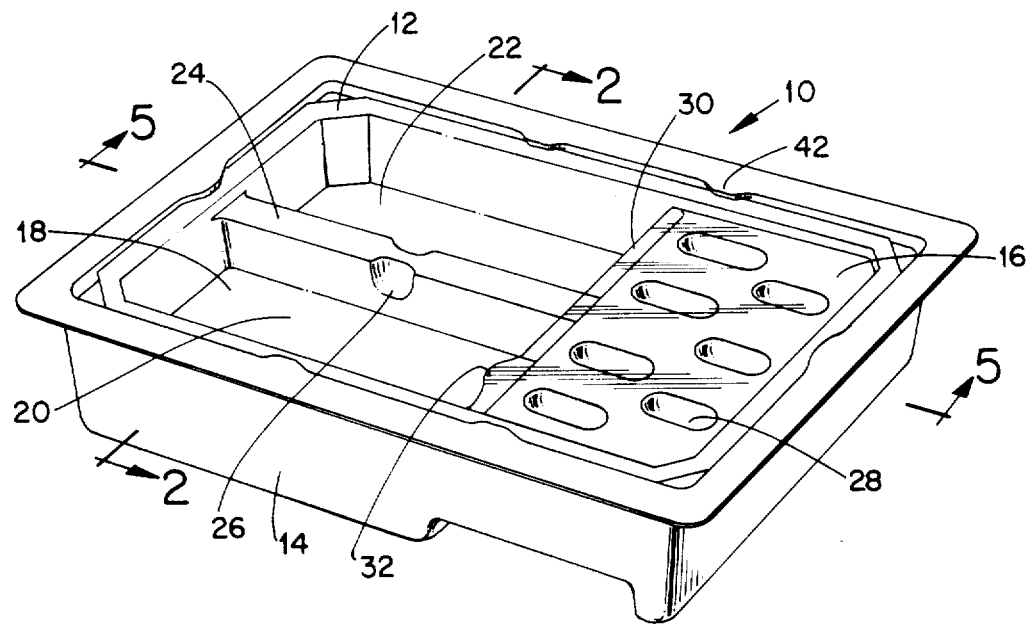
FIG. 1 is a pictorial view of the surgical kit of the subject invention.

Referring now more particularly to FIG. 1, there is provided surgical kit 10 which is formed from molded plastic and is particularly adapted to be used in conjunction with ophthalmological intraocular lens implantation surgery. Surgical kit 10 is completely disposable. A first or inner tray 12 is received inside of a second or outer tray 14. Inner tray 12 includes raised portion 16 and deep pan portion 18 which is divided into compartments 20 and 22 by raised shoulder 24. A pair of indentations 26 are provided on the top of raised portion 24 so that the user may readily grasp these indentations and remove the inner tray from the outer tray. Elevated portion 16 includes a plurality of embossments 28 which receive various surgical solutions and medicaments. For ophthalmological intraocular lens implantation surgery the following items could be included in the embossments 28: balanced salt irrigating solutions, intraocular lens, operative acetylcholine, anesthetic drops, a solution to protect the corneal endothelium, e.g. Healon, pilocarpine drops, plus the disposable parts and accessories for the irrigating and aspirating surgical unit which were provided in the prior art kit. A clear plastic cover 30 having tab 32 for easy removal covers the above-described items received in embossments 28 to stabilize the items. Compartment 20 of deep pan portion 18 of the tray normally would receive tubing for a lens suction device and plastic bagging. Compartment 22 normally would receive additional tubing, as well as cellulose sponges, syringes, a microscope cover, surgical mittens and other accessories. As stated previously, the above-described materials which are received in tray 12 are all normally utilized during lens implant surgery. As further seen in reference to FIG. 2, inner tray 12 includes walls 34 and 36. Lip 38 extends away from walls 34 and 36 and rests upon shoulder 40 on outer tray 14. The lip 38 is held in place on shoulder 40 by bead 42. A plurality of such beads are located about the inner periphery of outer tray 14. Shoulder 40 also extends about the inner periphery of tray 14, slightly below the level of bead 42. Thus the inner tray is snap-fitted into the outer tray. A paper cover 44 is received over the top of both the inner and outer tray and is sealed about its edges 46 by ultrasonic welding or some other suitable means.

Figure 4:
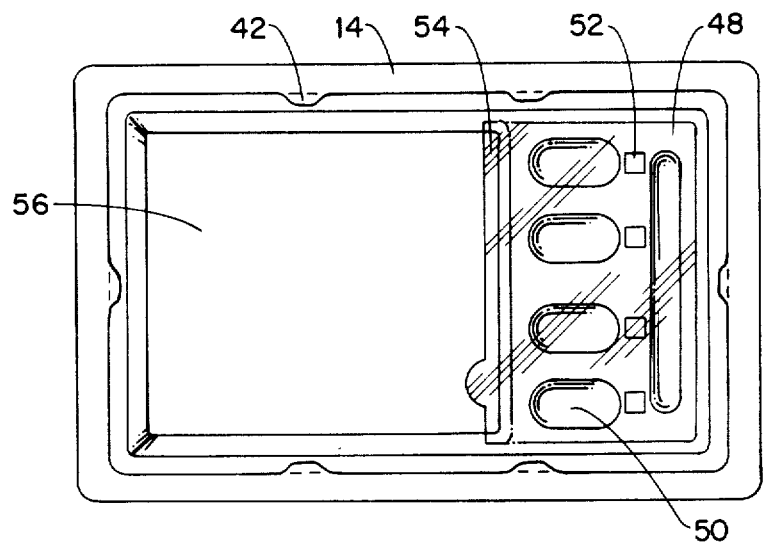
FIG. 4 is a top plan view of the other tray shown in FIG. 2.

Referring now to FIG. 4, outer tray 14 includes elevated section 48 which is somewhat similar to elevated section 16 of tray 12. Elevated section 48 includes a plurality of embossments 50 which are particularly adapted to receive postoperative medicaments and solutions. These postoperative materials are normally used by the patient himself. Color code symbols 52 which are adjacent to preselected embossments and have the same color code as the particular solution or medication bottles are provided to avoid confusion by the patient. The clear plastic cover 54 may be provided in the same fashion as the clear plastic cover 32 shown in FIG. 1 to stabilize the materials in the embossments. Tray 14 also includes deep pan portion 56 which extends substantially lower than elevated portion 48. Deep pan portion 56 also receives postoperative materials such as eye pads, tape and shields. Furthermore, additional materials may be inserted into deep pan portion 56, including the patient's personal belongings and other postoperative materials which the hospital may require for the patient to use subsequent to surgery, not only in his hospital room but also in his home.

Figure 2:
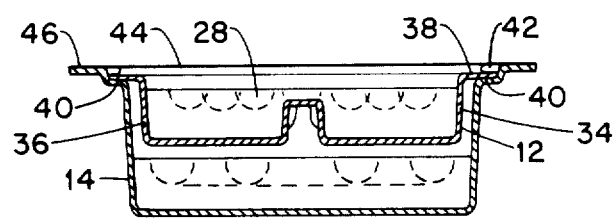
FIG. 2 is a sectional view of the surgical kit of FIG. 1 taken through section line 2—2.
Figure 3:
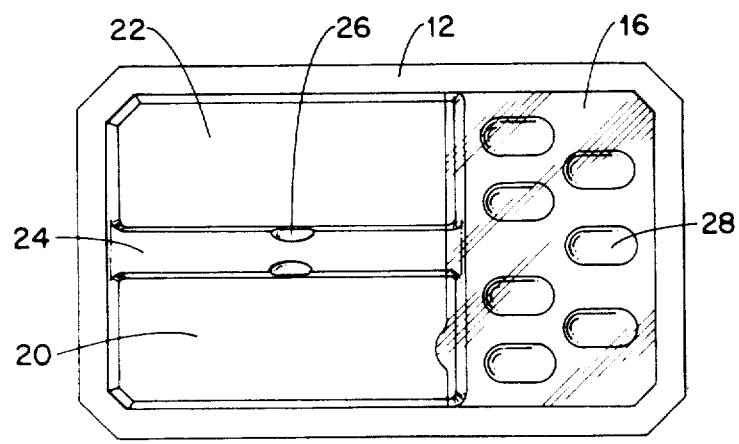
FIG. 3 is a top plan view of one of the trays shown in FIG. 2.
Figure 5:
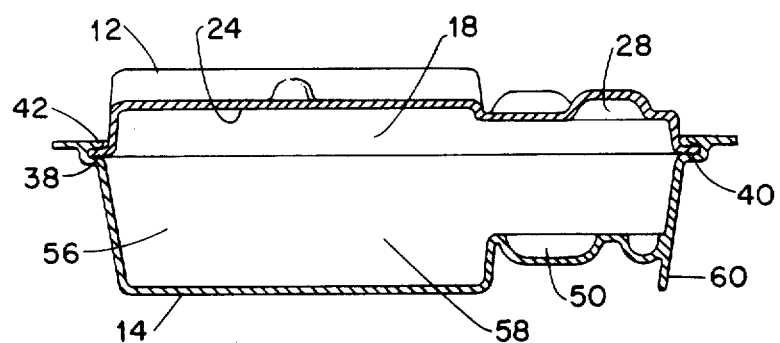
FIG. 5 is a sectional view of the kit of FIG. 1 taken through section line 5—5 except that the top tray has been flipped over.

Referring now to FIG. 5, with the former inner tray 12 flipped over 180° and reattached to outer tray 14 by snapping lip 38 under bead 42 and resting the lip on shoulder 40, a substantially greater volume displacement 58 is achieved inside of the container over the volume displacement obtained when pan 12 is received inside of pan 14 as shown in FIG. 2. It should be particularly noted that with deep pan portion 56 of pan 14 being aligned with deep pan portion 18 of pan 12, rather large articles may be placed inside the resulting container. In order to provide additional stability to the kit as it rests on a planer surface, leg 60 may be provided and projects from the elevated side of pan 14.

The above-described surgical kit should be utilized as follows. Operating room personnel first remove plastic cover 44 from the top of kit 10. Inner pan 12 is removed from outer pan 14 by grasping indentations 26. The materials received in deep pan portion 18 and the accessories and parts for the irrigating and asperating unit are put in place, cover 30 is removed from elevated portion 16 and the surgery begins utilizing the materials in embossment 28. After the surgery has been completed, some of the medications contained in embossments 50 of outer pan 14 are utilized by operating room personnel but then replaced into their respective embossments. Furthermore, some of the materials in deep pan portion 56 may also be utilized. Any additional required materials for postoperative care are placed in deep pan portion 56. The inner pan 12 is flipped over, that is, turned 180° and reattached to outer pan 14 as previously described. Thus the inner pan 12 becomes a cover for the outer pan 14. The newly formed container is then taken back to the patient's room and the materials contained therein are utilized for postoperative care both in the hospital and in the patient's home.

As can be seen from the above, a new surgical kit has been provided which contains portions for integrating surgical materials and postoperative supplies into the same kit. The kit is inexpensive to manufacture, is completely disposable, and enables the manufacturer to provide both surgical and postoperative in the same sterile package. Furthermore, in particularly for lens implant surgery, the kit may be personalized to the individual patient by the manufacturer in that the proper sized lens may be added to the kit at the factory. The patient's name may also be applied on a label on the outside of the kit either by the manufacturer or at the hospital.

From the foregoing description of the illustrative embodiment of the invention it will be apparent that many modifications may be made therein. It will be understood that this embodiment of the invention is intended as an exemplification of the invention only and that this invention is not limited thereto. It is also to be understood, therefore, that it is intended in the appended claims to cover all modifications that fall within the true spirit and scope of the invention.

I claim:

1. An improved surgical kit comprising:
   first and second trays, each having side walls and a bottom, at least a portion of the bottom of each tray having a raised portion including a plurality of embossments forming recesses therein receiving various medical supplies, the bottoms of said first and second trays each having a deep pan portion separate from said raised portion for receiving various articles, said deep pan portion in each tray displacing a larger volume than said embossments in the bottom of said respective first and second trays; said first tray having a lip extending away from its side walls about the outer periphery of said first tray; said second tray having a shoulder on its side walls about the inner periphery of said second tray, said shoulder receiving said lip whereby said first tray is adapted to be mounted on said second tray.

2. A kit as set forth in claim 1, further including means for retaining said lip against said shoulder such that said first and second trays are secured together.

3. A kit as set forth in claim 2, wherein said means for retaining includes a plurality of beads extending over said shoulder with a space being provided between said beads and said shoulder for receiving portions of said lip.

4. A kit as set forth in claim 2, wherein said walls of said first tray are aligned with and adjacent to portions of said walls of said second tray whereby said first tray is contained within said second tray.

5. A kit as set forth in claim 4, further including means for sealing said first and second trays from the outer environment, including a sealed cover over the top of said trays.

6. A kit as set forth in claim 2, wherein said walls of said first tray extend above walls of said second tray whereby said first tray is a cover for said second tray.

7. A kit as set forth in claim 6, wherein the volume of space displacement formed between the bottoms of said first and said second trays is substantially greater when said walls of said first tray extend above said walls of said second tray than when said walls of said first tray are aligned with and adjacent to portions of said walls of said second tray.

8. A kit as set forth in claim 1, further including means for removing said first tray from said second tray.

9. A kit as set forth in claim 8, wherein said means for removing includes a raised shoulder extending through a portion of said first tray and a pair of indentations in said shoulder for enabling the user to readily grasp said first tray.

10. A kit as set forth in claim 1, wherein said walls of each tray extend away from each other; said deep pan portions of each tray being aligned with one another whereby a substantial volume of space is displaced between said deep pan portions.

11. A kit as set forth in claim 1, further including a leg extending from said elevated portion of said second tray for providing additional stability to said kit.

12. A kit as set forth in claim 10, further including a cover provided over each of said elevated portions.

13. A kit as set forth in claim 1, further including color code means attached in the vicinity of at least a portion of said embossments in said second tray.

14. A method for utilizing a surgical kit formed with first and second trays each having side walls and a bottom, the bottom of each tray having a deep pan portion and a raised portion including a plurality of embossments forming recesses therein receiving various supplies, said deep pan portions being separate from said raised portions, said deep pan portions of said second trays each displacing a larger volume than said embossments of said respective first and second trays; said first tray having a lip extending away from its side walls about the outer periphery of said first tray, said second tray having a shoulder on its side walls about the inner periphery of said second tray, said shoulder receiving said lip whereby said first tray is first mounted within said second tray comprising the steps of:

removing said first tray from said second tray, removing surgical supplies from said first tray, performing surgery utilizing at least a portion of said surgical supplies in said first tray, flipping said first tray to its side opposite the side in which it was received inside said second tray, aligning said deep pan portions of said first and second trays with one another, attaching said first tray in its flipped condition to said second tray whereby an enclosure is provided between said first and said second trays.

15. A method as set forth in claim 14, further including the step of adding additional surgical materials to said second tray prior to flipping said first tray for use after surgery.

* * * * *